(12) United States Patent
Muhle et al.

(10) Patent No.: US 7,947,797 B2
(45) Date of Patent: May 24, 2011

(54) METHOD FOR OPERATING A GAS-PHASE REACTOR AT OR NEAR MAXIMUM PRODUCTION RATES WHILE CONTROLLING POLYMER STICKINESS

(75) Inventors: Michael E. Muhle, Kingwood, TX (US); Robert O. Hagerty, La Porte, TX (US)

(73) Assignee: Univation Technologies, LLC, Houston, TX (US)

( * ) Notice: Subject to any disclaimer, the term of this patent is extended or adjusted under 35 U.S.C. 154(b) by 569 days.

(21) Appl. No.: 11/227,710

(22) Filed: Sep. 14, 2005

(65) Prior Publication Data
US 2007/0060721 A1   Mar. 15, 2007

(51) Int. Cl.
C08F 210/00 (2006.01)
C08F 10/14 (2006.01)
C08F 4/72 (2006.01)
C08F 4/00 (2006.01)

(52) U.S. Cl. .... 526/348; 526/90; 526/348.3; 526/348.4; 526/348.5; 526/170

(58) Field of Classification Search ............... 526/348, 526/901, 90, 348.3, 348.4, 348.5, 170
See application file for complete search history.

(56) References Cited

U.S. PATENT DOCUMENTS

| 4,543,399 A * | 9/1985 | Jenkins et al. ............... 526/70 |
| 4,588,790 A | 5/1986 | Jenkins, III et al. |
| 4,803,251 A | 2/1989 | Goode et al. |
| 5,352,749 A | 10/1994 | DeChellis et al. |
| 5,405,922 A | 4/1995 | DeChellis et al. |
| 5,408,882 A | 4/1995 | McKinley et al. |
| 5,436,304 A | 7/1995 | Griffin et al. |
| 6,122,557 A | 9/2000 | Harrell et al. |
| 6,301,546 B1 | 10/2001 | Weinstein et al. |
| 6,336,353 B2 | 1/2002 | Matsiev et al. |
| 6,460,412 B1 | 10/2002 | Cai et al. |

FOREIGN PATENT DOCUMENTS

| CN | 1544140 A | 11/2004 |
| EP | 00233787 | 8/1990 |
| EP | 0399796 | 3/1994 |
| EP | 0385788 | 12/1994 |
| WO | WO 0109196 | 2/2001 |
| WO | WO 03051929 | 6/2003 |
| WO | WO 2007/005528 | 1/2007 |

OTHER PUBLICATIONS

"Process Analysis & Automation Acoustic Emission Technology a New Sensing Technique for Optimising Polyolefin Production", copyright 2000.*

(Continued)

Primary Examiner — William K Cheung

(57) ABSTRACT

Embodiments of the present invention relate to operating a gas-phase reactor at or near maximum production rates and to measuring and controlling polymer stickiness in a gas phase reactor polymerization. In particular, embodiments relate to monitoring acoustic emissions in a reactor during gas phase polymerization to determine the onset of reactor stickiness and possibly discontinuity events such as chunking and sheeting resulting from that stickiness. Embodiments also relate to monitoring acoustic emissions to determine the need for effective control of parameters that minimize reactor stickiness and thereby preventing discontinuity events. The emissions are processed by arithmetic averaging.

14 Claims, 4 Drawing Sheets

Pilot Scale Fluidized Bed Reactor

OTHER PUBLICATIONS

Anonymous, "*Reactor Sheering Detection Using Ultrasonic Interferometry and Acoustic Emission Analysis,*"0 *IP.COM Journal.* IP.Com Inc., West Henrietta, NY, US, (Jun. 2, 2003).

Powder Technology 7, pp. 285-292 (1973).

Process Analysis & Automation, "Application Notes 2002-112" Acoustic Emission Terms and Definitions, 2002.

Process Analysis & Automation "Acoustic Emission Technology a New Sensing Technique for Optimising Polyolefin Production" copyright 2000.

Process Analysis & Automation "Application Note/111 Agglomeration Detection by Acoustic Emission", 2002.

Bakkar, A., et al., Design Reactors via CFD, Chemical Engineering Progress, Dec. 21, 2001 vol. 97, No. 12, pp. 30-39, Abstract; p. 30.

* cited by examiner

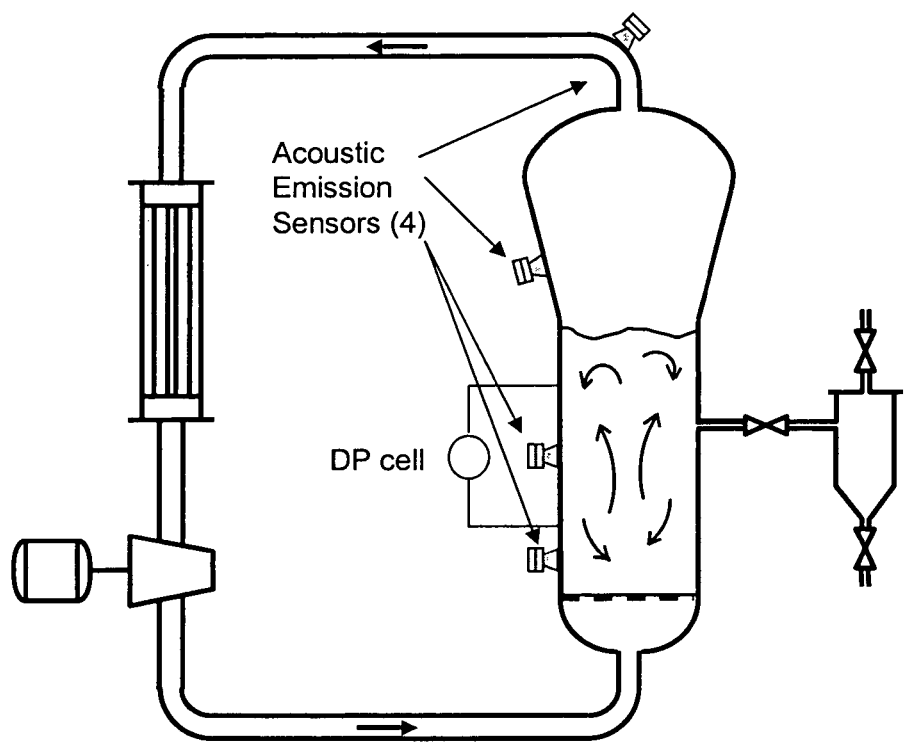
Figure 1 – Pilot Scale Fluidized Bed Reactor

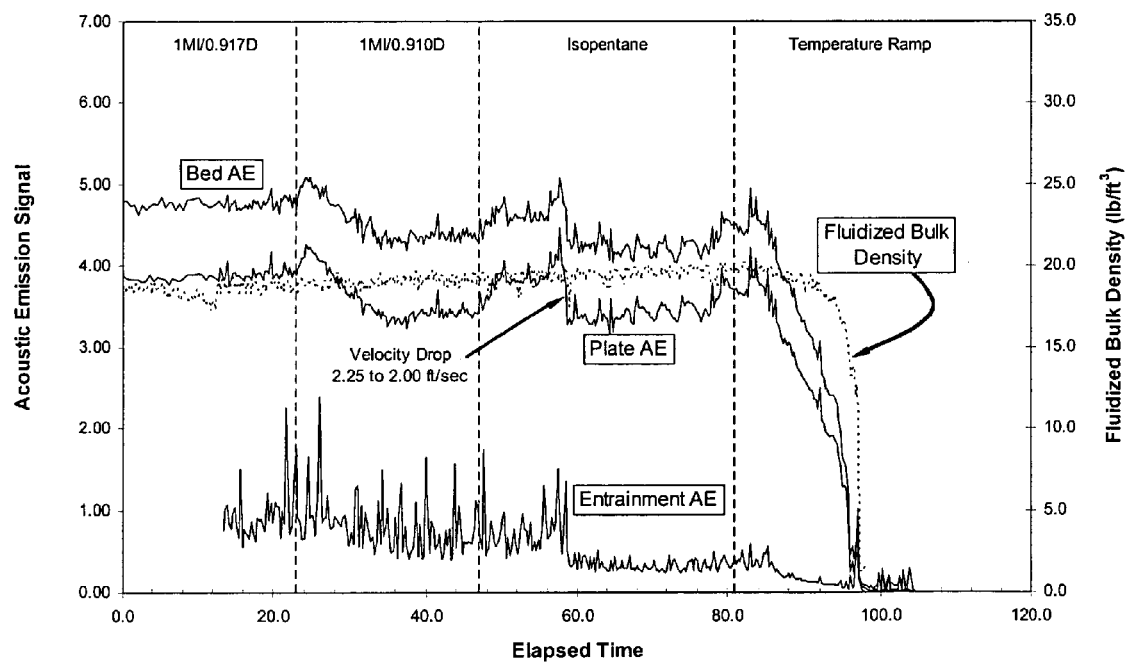

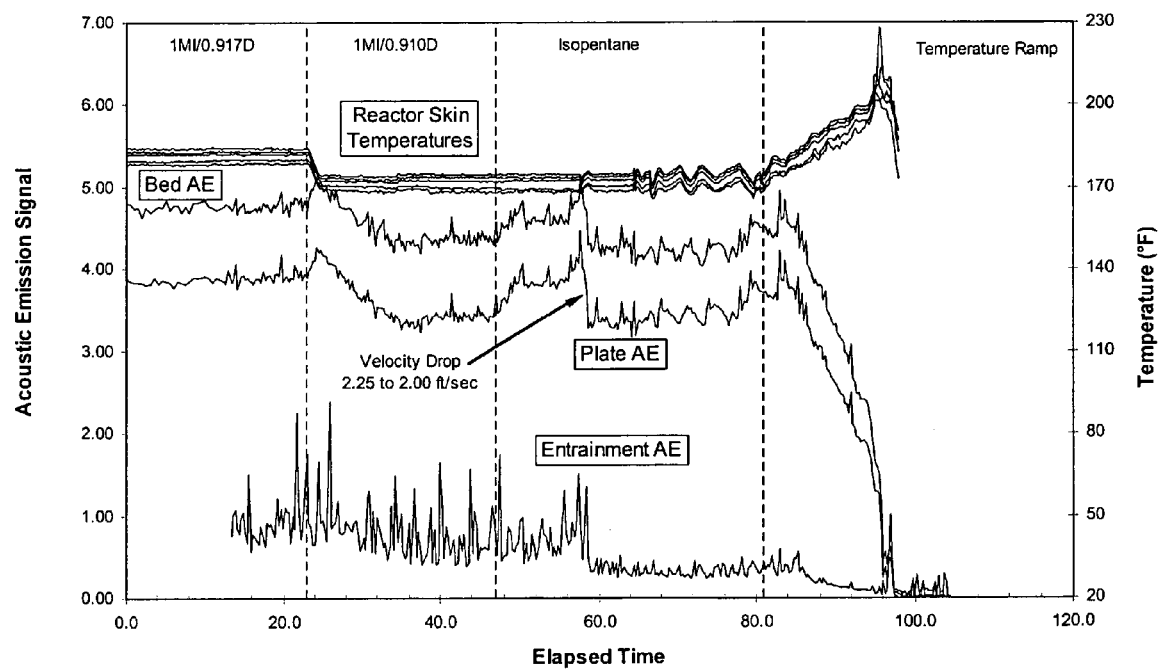

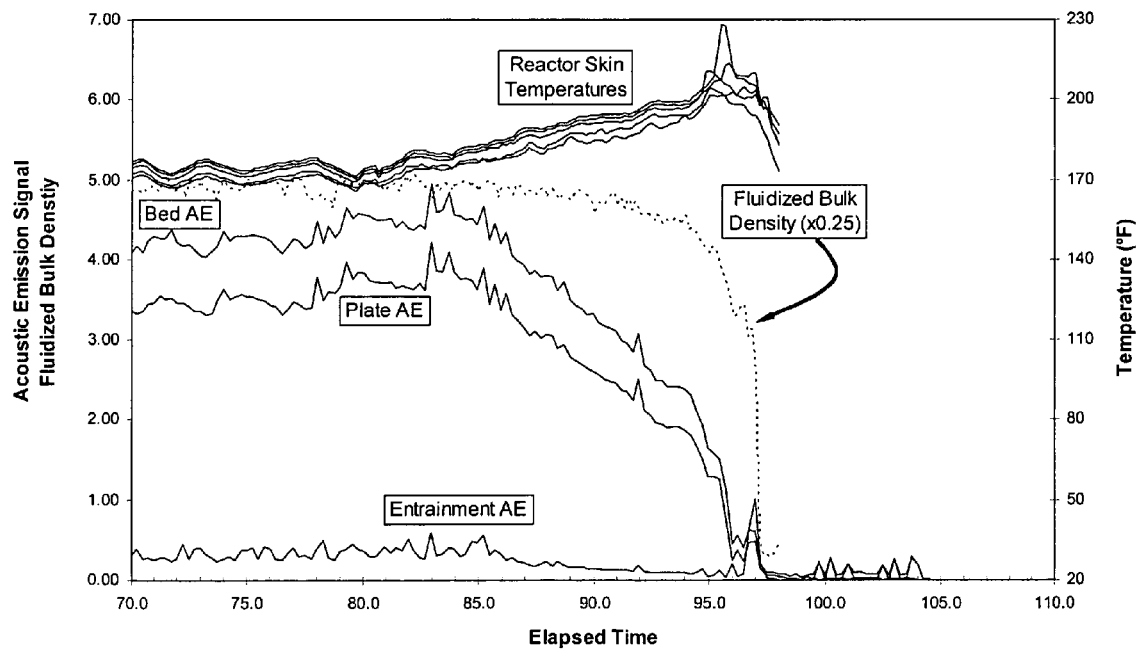
Figure 4 – Acoustic Emission, Fluidized Bulk Density and Reactor Temperature Plot

METHOD FOR OPERATING A GAS-PHASE REACTOR AT OR NEAR MAXIMUM PRODUCTION RATES WHILE CONTROLLING POLYMER STICKINESS

TECHNICAL FIELD

Embodiments of this invention relate to operating a gas-phase reactor at or near maximum production rates and to monitoring and controlling incipient stickiness of polymer particles in gas phase polymerization reactors, and controlling resultant polymer particle agglomeration caused by this stickiness, that if left unchecked, may further result in a reactor shutdown.

BACKGROUND

Generally in a gas-phase fluidized bed process for producing polymers from monomers, a gaseous stream containing one or more monomers is continuously passed through a fluidized bed under reactive conditions in the presence of a catalyst. This gaseous stream is withdrawn from the fluidized bed and recycled back into the reactor. Simultaneously, polymer product is withdrawn from the reactor and new monomer is added to replace the polymerized monomer. The recycled gas stream is heated in the reactor by the heat of polymerization. This heat is removed in another part of the cycle by a cooling system external to the reactor.

It is important to remove heat generated by the reaction in order to maintain the temperature of the gaseous stream inside the reactor at a temperature below the polymer melting point and/or catalyst deactivation temperature. Further, heat removal is important to prevent excessive stickiness of polymer particles that if left unchecked, may result in loss of fluidization or agglomeration of the sticky particles which may lead to formation of chunks or sheets of polymer that cannot be removed as product. Further, such chunks or sheets may fall onto the distributor plate causing impaired fluidization, and in many cases forcing a reactor shutdown. The prevention of such stickiness has been accomplished through controlling the temperature of the gaseous stream in the reaction bed to a temperature below the fusion or sintering temperature of the polymer particles produced during the polymerization reaction. Above this fusion or sintering temperature, empirical evidence suggests that such fusion or sintering leads to agglomeration or stickiness, which in turn can, if left unchecked, may lead to the above conditions.

It is understood that the amount of polymer produced in a fluidized bed polymerization process is directly related to the amount of heat that can be withdrawn from a reaction zone in a fluidized bed within the reactor. Conventionally, heat has been removed from the gaseous recycle stream by cooling the recycle stream outside the reactor. A requirement of a fluidized bed process is that the velocity of the gaseous recycle stream be sufficient to maintain the reaction zone in a fluidized state. In a conventional fluidized bed polymerization process, the amount of fluid circulated to remove the heat of polymerization is greater than the amount of fluid required for support of the fluidized bed and for adequate mixing of the solids in the fluidized bed. The excess velocity provides additional gas flow to (and through) the fluid bed for additional cooling capacity and more intensive mixing of the reactor bed. However, to prevent excessive entrainment of solids in a gaseous stream withdrawn from the fluidized bed, the velocity of the gaseous stream must be regulated. Also, in a steady state fluidized bed polymerization process wherein the heat generated by the polymerization reaction is proportional to the rate of polymer production, the heat generated is equal to the heat absorbed by the gaseous stream and lost by other means, such that the bed temperature remains constant.

For a time, it was thought that the temperature of the gaseous stream external to the reactor, otherwise known as the recycle stream temperature, could not be decreased below the dew point of the recycle stream. The dew point of the recycle stream is that temperature at which liquid condensate first begins to form in the gaseous recycle stream. The dew point can be calculated knowing the gas composition and is thermodynamically defined using an equation of state. It was believed that condensed liquid in the recycle stream would inevitably result in plugging of the recycle stream lines, the heat exchanger, the area below the fluidized bed and especially the gas distributor plate. As a consequence of operating at a temperature above the dew point of the recycle stream to avoid the expected problems associated with liquid being in the gaseous recycle stream, production rates in commercial reactors could not be significantly increased without enlarging reactor diameters for increased heat removal capability. There was also concern that excessive amounts of liquid in the recycle stream would disrupt the fluidization process to the extent that the fluidized bed would collapse resulting in the sintering of solid polymer particles into a solid mass causing the reactor to shut down.

Contrary to this belief, as suggested by Jenkins, et al. in U.S. Pat. No. 4,543,399 and related U.S. Pat. No. 4,588,790 a recycle stream can be cooled to a temperature below the dew point in a fluidized bed polymerization process resulting in condensing a portion of the recycle gas stream. The disclosures of these two Jenkins patents are incorporated herein by reference. The resulting stream containing entrained liquid is then returned to the reactor without causing the aforementioned agglomeration and/or plugging phenomena (which had been expected prior to Jenkins). This process of purposefully condensing a portion of the recycle stream is known in the industry as a "condensed mode" operation in a gas phase polymerization process.

The above-mentioned U.S. patents to Jenkins et al. suggest that when a recycle stream temperature is lowered to a point below its dew point in "condensed mode" operation, an increase in polymer production is possible, as compared to production in a non-condensing mode because of increased cooling capacity. Also, Jenkins, et al. found that a substantial increase in space time yield, the amount of polymer production in a given reactor volume, can be achieved by operating in "condensed mode" with little or no change in product properties.

Cooling of the recycle stream to a temperature below the gas dew point temperature produces a two-phase gas/liquid mixture with solids contained in both of these phases. The liquid phase of this two-phase gas/liquid mixture in "condensed mode" operation remains entrained or suspended in the gas phase of the mixture. Vaporization of the liquid occurs only when heat is added or pressure is reduced. In the process described by Jenkins, et al., vaporization occurs when the two-phase mixture enters the reactor. The increase in space time yields achieved by Jenkins, et al. are the result of this vaporization, and also the increased temperature differential between the entering recycle stream and the fluidized bed temperature. Both of these factors increase the heat removal capability of the system and thereby enable higher space time yields (higher reactor production rates).

Jenkins, et al. illustrate the difficulty and complexity of such reactor control in general, and of trying to extend the stable operating zone to optimize the space time yield in a gas phase reactor, especially when operating in condensed mode.

The cooling capacity of the recycle gas can be increased further while at a given reaction temperature and a given temperature of the cooling heat transfer medium. One option described is to add non-polymerizing, non-reactive materials to the reactor, which are condensable at the temperatures encountered in the process heat exchanger. Such non-reactive, condensable materials are collectively known as induced condensing agents (ICAs). Increasing concentrations of ICA in the reactor causes corresponding increases in the dew point temperature of the reactor gas, which promotes higher levels of condensing for higher (heat transfer limited) production rates from the reactor. Suitable ICA materials are selected based on their specific heat and boiling point properties. In particular, the ICA compound is selected such that a relatively high portion of the material is condensed at the cooling water temperatures available in polymer production plants, which are typically 20-40° C. Such ICA materials include hexane, isohexane, pentane, isopentane, butane and isobutane.

Recognition that high concentrations of condensable gases, either ICA, comonomers or combinations thereof, can cause the polymer in the fluid bed to become sticky can be found in U.S. Pat. No. 5,352,749 (DeChellis). When either or both of these condensable materials are present, the reactor contents, specifically the polymer contents, can become sticky because these condensable materials are highly soluble in the polymer particles. When the condensable concentrations are higher than acceptable levels they effectively lower the polymer melting point, and stickiness can result. The same effect can be the result of increasing reactor temperature in the absence of excess concentrations of condensable components, or the result of combinations of increased reactor temperature and high concentrations of condensable components (either or both of ICA and/or comonomer).

In the '749 document, and in U.S. Pat. Nos. 5,405,922 and 5,436,304, the ICA is at relatively high concentrations to thereby increase heat removal capacity of the system based on the latent heat of vaporization associated with the ICA or liquid monomer. Upper limits of ICA in the reactor are discussed, depending on the type of polymer being produced. Attempts to go beyond such levels caused the fluid bed or, more specifically, the polymer particles suspended in the fluid bed, to become cohesive or "sticky", and in some cases caused the fluid bed to solidify in the form of a large chunk. The stickiness problem is characterized by undesirable changes in fluidization and mixing in the fluid bed, which if left unchecked, may develop into a reactor discontinuity event, such as sheeting in the straight sided reaction section, sheeting in the dome of such a reactor or chunking, any of which can lead to a reactor shut-down, which in large scale reactors are expensive. These solid masses of polymer (the sheets or chunks) eventually become dislodged from the walls and fall into the reaction section and settle on the distributor plate, where they interfere with fluidization, block the product discharge port, and usually force a reactor shut-down for cleaning, any one of which can be termed a "discontinuity event", which in general is a disruption in the continuous operation of a polymerization reactor. The terms "sheeting and/or chunking" while used synonymously herein, may describe different manifestations of similar problems, in each case they can lead to a reactor discontinuity event.

In U.S. Pat. No. 5,352,749, the authors determined that a limiting concentration of ICA (isopentane) existed, beyond which the reactor contents would suddenly loose fluidization. The authors characterized this limit by tracking the ratio of fluidized bulk density to settled bulk density. As the concentration of isopentane was increased, they found that the bulk density ratio steadily decreased. When the concentration of isopentane was sufficiently high, corresponding to a bulk density ratio of 0.59, they found that fluidization in the reactor was lost. They therefore determined that this ratio (0.59) was a point of no return, below which the reactor will cease functioning due to loss of fluidization. Although this was not appreciated by the authors of U.S. Pat. No. 5,352,749, the sudden loss in fluidization at relatively high ICA concentrations was due to the formation of sticky polymer.

Two articles by Process Analysis & Automation Limited (PAA) ("Agglomeration Detection by Acoustic Emission" PAA Application note: 2002/111 © 2000; and "Acoustic Emission Technology—a New Sensing Technique for Optimising Polyolefin Production" © 2000), suggest process control in fluidized bed production of polyolefins utilizing acoustic emission sensors located at various positions on the reactor and recycle piping. These publications purport to solve the problem of detection of large polymer agglomerates in the reactor, such as chunks or sheets, rather than the detection of stickiness of the resin particles, as provided by embodiments of the present invention. The PAA documents provide only one specific example, showing the detection of a chunk of approximately 1.5 meters in diameter within a commercial fluid bed reactor. There is no mention of the detection of polymer stickiness or cohesiveness. In effect, the PAA documents describe the detection of agglomerates after they have been formed in the reactor, rather than the detection of resin stickiness that, if left unchecked, could lead to the formation of the agglomerates. Additionally, the PAA documents suggest that the presence of agglomerates is indicated by an increase in acoustic emission signal intensity (presumably by recording the noise generated when the relatively large chunks of polymer strike the walls of the reactor). In contrast, embodiments of the present invention teach that increasing levels of resin stickiness are indicated as decreases in acoustic emission signal intensity.

Chinese application 200310113358.7 purports to solve the problem of determining particle size distribution through (acoustic) signal decomposition. Detection of large agglomerates is discussed, of 22 mm particle size. No specific corrective action is suggested to address the problem (or problems) that create the polymer agglomerates.

WO 03/051929 (incorporated herein by reference), describes the use of mathematical chaos theory to detect the onset and presence of sheeting in a fluid bed reactor. Signals from a range of instruments, including acoustic emission sensors, differential pressure sensors, static sensors, and wall temperature sensors are filtered by certain specified methods to construct a "time-series" of data, which is then processed by methods of non-linear dynamics herein referred to as chaos theory and compared to data from a control reactor running without sheeting. The onset of sheeting is indicated by an increase in mean "cycle time" (relative to the control reactor), usually with a concurrent decrease in the "mean deviation" of the time-series. Alternatively, the onset of sheeting is indicated by a decrease in the mathematical "entropy" of the time-series data, as compared to a similar reactor running without sheeting. (The terms "time-series", "cycle time", "mean deviation", and "entropy" refer to calculated parameters defined by chaos theory.) There is no disclosure of the use of acoustic emission sensors to determine conditions of impending stickiness in the reactor, nor is there a disclosure of the use of these sensors to provide information relevant to distributor plate fouling. There is no disclosure of the use of simple averages and standard deviations of the acoustic emission readings (without recourse to the complexities involved with chaos theory), and there is no disclosure of the use of these sensors (or any other methods) to allow safe operation of a reactor near its limit of ultimate cooling capacity for maximum production rates.

Adding to the complexity of control of stickiness while using ICAs, different polymer products vary widely in their ability to tolerate such ICA materials, some having a relatively high tolerance (expressed in partial pressure of the ICA in the reactor), e.g. 50 psia, while other polymers may tolerate as little as 5 psia, and in these latter polymers, the heat transfer limited production rates, under similar conditions, are substantially lower. Polymers which possess a more uniform comonomer composition distribution are known to have a higher tolerance to the partial pressure of the ICA in the reactor. Metallocene catalyst produced polymers are a good example of polymers with such a more uniform comonomer composition. However, at some point even these metallocene produced polymers reach a limiting ICA concentration that induces stickiness. The limiting ICA concentration depends on several factors in addition to the polymer type, and include reactor temperature and comonomer type and concentration. Further, with the effect of temperature, ICA level and comonomer levels all affecting on the onset of stickiness, determining the point at which sticking begins to occur has been heretofore been difficult.

Even within the constraints of conventional, safe operation, control of such reactors is complex adding further to the difficulty and uncertainty of experimentation if one wishes to find new and improved operating conditions that might result in higher production rates.

Large scale gas phase plants are expensive and highly productive. Risks associated with experimentation in such plants are high because downtime is costly. Therefore it is difficult to explore design and operating boundaries experimentally in view of the costs and risks.

It would be desirable to provide a method of determining a stable operating condition for gas fluidized bed polymerization, especially if operating in condensed mode, to facilitate optimum design of the plant and the determination of desirable process conditions for optimum or maximum production rates in a given plant design.

It would also be desirable to have a mechanism in commercial gas-phase reactors to detect the onset of stickiness that is a better indicator, or an earlier indicator of the onset of stickiness than the conventional technique of monitoring the fluidized bulk density (as described in U.S. Pat. No. 5,352,749) or other methods, allowing operators to determine when excessive sticking is occurring and enabling those operators to take corrective action, while keeping the reactors at or near this optimum production rate point, permitting higher production rates with substantially less risk.

SUMMARY

Among our contemplated embodiments are a process for operating a gas-phase reactor at or near maximum production rates, under condensed mode reactor conditions, comprising feeding monomers and at least one catalyst to the gas-phase reactor, to make polymer particles; feeding at least one induced condensing agent (ICA) to the gas-phase reactor measuring and processing acoustic emissions of the polymer particles in the gas-phase reactor; and controlling the reactor at or near maximum production rate for a given polymer, by the measuring of the acoustic emissions, such that when the acoustic emissions deviate from acoustic emissions of a steady state reactor producing the same given polymer, by more than one (negative) standard deviation, the controlling comprises a corrective action comprising: adjusting one of ICA level, comonomer level, reactor temperature or combinations thereof; wherein the processing of the signal comprises arithmetic averaging using acoustic emissions signal sampled from a time window in the range of 0.01-1000 seconds, where the sampling frequency ranges from 0.01-1000 samples per second.

Also contemplated is a process of producing an ethylene copolymer in a gas phase reactor at or near maximum production rates for the ethylene copolymer, comprising: maintaining a signal or signals of one or more acoustic emissions sensors located on a cylindrical section of the reactor, in the range of zero to minus three (−3) standard deviations of the signals of the one or more acoustic emissions sensors, from the signal of the acoustic emission sensors at steady state conditions in the reactor. Additionally contemplated is a process for monitoring stickiness of polymer particles in a gas-phase, fluid-bed polymerization reactor, comprising feeding ethylene and a comonomer selected from one or more of 1-butene, 1-hexene or 1-octene and a metallocene catalyst; one or more of an ionic activator, an alumoxane or a modified alumoxane, to the reactor feeding an induced condensing agent (ICA) to the reactor measuring acoustic emission signal or signals of the particles using at least one acoustic emission sensor on the exterior of the reactor, wherein the at least one acoustic emission sensor is located on an exterior cylindrical section of the reactor, at a point between the first 0.25 reactor diameters above a reactor distributor plate, and below the first 0.25 reactor diameters below a cylindrical-conical junction of the reactor, wherein the signals comprise processing of the signal using an arithmetic averaging using the acoustic emissions signal sampled from a time window in the range of 0.01-1000 seconds, where the sampling frequency ranges from 0.01-1000 samples per second; and adjusting one of ICA level, comonomer level, reactor temperature or combinations thereof, when the signal deviates at least three standard deviations negatively from an acoustic signal or signals of the process at steady state conditions when producing the same reactor polymer.

DESCRIPTION OF THE DRAWINGS

FIG. 1 shows a schematic of a typical gas-phase reactor with various probes located in different sections of the reactor and recycle line.

FIG. 2 shows acoustic emission readings during experimental runs, with a fluidized bed density (FBD) overlay.

FIG. 3 shows acoustic emission readings during experimental runs, with a temperature overlay.

FIG. 4 shows acoustic emission readings during experimental runs, with a temperature ramp.

DESCRIPTION

We have surprisingly discovered that by monitoring the acoustic emissions in a polymerization reactor we can detect the onset of reactor polymer particle stickiness and therefore prevent the problems associated with excessive stickiness much more effectively and earlier than with other conventional sensors or other methods disclosed herein, while permitting operating the reactor at or near maximum production rates for each polymer. Other embodiments of this invention relate to monitoring stickiness in gas phase polymerization reactors utilizing any catalyst type, such as metallocene catalysts either alumoxane and/or non-coordinating anion activated; so-called "conventional" Zeigler-Natta catalysts; or chromium catalysts ("Phillips" catalysts); by monitoring acoustic emissions in the fluid bed to determine the onset of reactor stickiness.

More importantly, by monitoring the acoustic emissions of a reactor through one or more acoustic emission sensors, reactors can be made to be more efficient (higher production rates) by running the reactors with higher levels of the ICA component closer to the point where stickiness may begin, than has been previously possible, due to the ability to pinpoint when a reactor (and its contents) are approaching the limiting of point stickiness, demonstrated by a less intense acoustic emission signature from the reactor contents.

Sheeting and/or Chunking

Stickiness can lead to reactor sheeting or chunking or both. There are at least two distinct forms of sheeting that occur in gas phase reactors. The two forms (or types) of sheeting are described as wall sheets or dome sheets, depending on where they are formed in the reactor. Wall sheets are formed on the walls (generally vertical sections) of the reaction section. Dome sheets are formed much higher in the reactor, on the conical section or on the hemispherical head on the top of the reactor (FIG. 1).

When sheeting occurs with Ziegler-Natta catalysts, it generally occurs in the lower section of the reactor and is referred to as wall sheeting. Ziegler-Natta catalysts are capable of forming dome sheets, but the occurrence is rare. With metallocene catalysts, sheeting can occur in either location or both locations; that is, both wall sheeting and dome sheeting can occur. Chromium or "Phillips" catalysts are also prone to dome sheeting. Dome sheeting has been particularly troublesome with metallocene catalyst systems. Typical metallocene compounds are generally described as containing one or more ligands capable of bonding to the transition metal atom, usually, cyclopentadienyl derived ligands or moieties, in combination with a transition metal selected from Group 4, 5 or 6 or from the lanthanide and actinide series of the Periodic Table of Elements.

Reactor chunking occurs when one or more sections of the reactor lose effective fluidization or mixing. Without adequate mixing, the rate of heat removal from these sections is diminished. With the diminished heat removal and continued reaction in these sections, overheating of the polymer can result. The overheating can cause agglomeration or melting or agglomeration of the polymer material, which results in the formation of solid masses, or chunks of polymer. In some cases (such as that described by DeChellis in U.S. Pat. No. 5,352,749) fluidization and mixing can be lost throughout the entire fluid bed, resulting in a large chunk comprising essentially all of the reactor contents.

Polymer stickiness is thus a root cause of the three types of discontinuity events described. The stickiness may be described as an increased "tackiness" or cohesiveness of the individual polymer particles. Significant increases in stickiness cause fundamental changes in fluidization within the reactor. These changes may be described in terms of the well known Geldart classification of particles (Powder Technology, 7, 285-292, 1973, the entire contents of which are herein incorporated by reference). Fluidized bed polymerization reactors normally operate as Geldart Group B particle beds, in which the relatively non-cohesive particles allow the formation of bubbles when the fluidizing gas velocity exceeds the minimum fluidizing velocity. These bubbles promote material mixing within the fluid bed and the dissipation of heat from the reacting particles within the fluid bed. A significant increase in particle stickiness, or cohesiveness, causes a transition to a Geldart Group C particle bed. In contrast to Group B particle beds, Group C beds tend to be cohesive, are difficult to fluidize, and tend to form flow channels rather than distinct bubbles that promote solids mixing. If the cohesiveness associated with Geldart Group C particles becomes pronounced, fluidization can be lost entirely, with the gas flow passing through the bed as an essentially solids-free flow channel. It is this limiting case of pronounced stickiness that can cause the discontinuity events discussed above. In general, our embodiments provide for determination of particle stickiness above Geldart Group C, in Geldart Group B.

In this context, the point of limiting stickiness is defined as the degree of polymer stickiness, or cohesiveness, that causes disruptions fluidization (and a resultant loss in mixing) sufficient to promote any of the discontinuity events of wall sheeting, dome sheeting and/or reactor chunking. Embodiments of our invention provide a means of detecting onset of increasing stickiness conditions prior to the initiation of these discontinuity events.

For gas phase polymerizations operating in condensed mode, significant stickiness results from increasing reactor temperature and/or increasing the presence of induced condensing liquids and/or increasing levels of comonomer, any of which, or combinations thereof, can result in higher productivity, to at or near maximum production rates for a given polymer in a given reactor. In the past, it has been necessary to maintain these parameters of the process within comparatively conservative ranges to avoid conditions that would induce stickiness in the reactor product and the resulting consequences. However, our method of determination of stickiness permits the operator of such processes to push the process/reactor to more efficient production regimes without concern that a stickiness event will go undetected and result in a reactor discontinuity event. Such reactor discontinuity events are costly production interruptions. The determination, by acoustic emission, of the state of stickiness in the reactor, permits the prevention, reduction or elimination of the excessive stickiness through actions on the part of a reactor's operators. These actions include reducing the ICA and/or comonomer concentration in the reactor gas phase, and/or reducing reactor temperature, or combinations thereof. The use of conventional differential pressure measurements (DP) (used to measure fluidized bulk density) provides warning of impending stickiness much later, as compared to the presently described acoustic emission sensor measurements. The acoustic emissions of the particles can be measured and the stickiness controlled using the means discussed herein, which in turn will prevent, reduce or eliminate reactor stickiness.

Detection of stickiness in the fluid bed may be carried out through the use of one or more acoustic emissions sensors. The acoustic emission sensors may be positioned on the cylindrical portion of the reactor. The one or more acoustic emission sensors may be placed on any part of the cylindrical section from the top of the distributor plate to the junction of the vertical/cylindrical wall with the conical section of the reactor, or that excludes the first 0.05, 0.1, 0.15, 0.2 or 0.25 reactor diameters above the distributor plate, and/or that excludes the first 0.05, 0.1, 0.15, 0.2 or 0.25 reactor diameters below the cylindrical-conical junction.

Detection of stickiness is accomplished by monitoring a running average of readings from one or more acoustic emission sensors located on the straight section of the reactor, adjacent to the fluid bed. The running average readings are calculated using the well known method of "moving time window" averaging. The average is defined as the sum of n individual readings in the time window divided by n.

$$\overline{X} = \frac{\sum_{i=1}^{n} X_i}{n}$$

where $\overline{X}$ is the current value of the running average and $\overline{X}_i$ is an individual reading. The n individual sample points in the formula above are preferably collected at equally spaced time intervals within the window.

Suitable time windows for the time window averaging are 0.01 to 1000 seconds, or 0.1-750 seconds, or 1 to 500 seconds. A significant increase in resin stickiness is indicated by a significant decrease in the running average signal from one or more acoustic emission sensors located on the reactor straight section, adjacent to the fluid bed. A significant decrease in the running average of an acoustic emission reading is defined herein as a decrease of one or more standard deviations of that signal. The standard deviation is computed by the following well known formula:

$$s^2 = \frac{\sum_{i=1}^{n}(X_i - \overline{X})}{(n-1)}$$

where s is the standard deviation, $X_i$ is an individual reading of an acoustic emission sensor within the window, n is the total number of observations, and $\overline{X}$ is the running average of the acoustic emission signal, described above. The number of sample points used in the calculation of standard deviation is equal to the number of sample points involved in the calculation of the running average. If, for example, the time window for computing the running average is 60 seconds, and the sampling frequency is 10 points per second, then n is equal to 600. In addition, sample points $\overline{X}_i$ used in the calculation of the standard deviation may be the same as those used in the calculation of the running average (i.e. the same sample windows are used in both calculations).

Suitable sampling frequencies for the acoustic emission sensors for use in the calculations of running averages and standard deviations described above may be from 0.01 to 1000 samples per second, or 0.1-750 seconds, or from 1 to 500 samples per second. The total number of samples n involved in the calculations (equal to the product of the window width and the sampling frequency) should be from 10 to 100,000 or from 50 to 10,000.

Note that the calculation of averages and standard deviations discussed above, do not employ non-linear methods of manipulating the acoustic emission signal, such as "cycle-time", and/or "mean deviation", do not employ mathematical chaos theory, are not "demodulated" to construct a "time series", nor is mathematical "entropy" used. In fact, the calculation of averages and standard deviations of the acoustic emission signal(s) from the one or more acoustic emission sensors, as applied herein, represent conventional methods of signal analysis that are well known to those skilled in the art.

The one or more acoustic emission sensors may be mounted on the exterior of the reactor, adjacent to the fluid bed.

We have surprisingly found that when the stickiness of reactor contents is increasing, the level of acoustic emissions in the fluidized portion of the bed disclosed above decreases. (In terms of its acoustic emissions signal, the bed effectively gets "quieter".) This discovery provides a relatively sensitive indication of increasing stickiness in the fluid bed, such conditions if left unchecked, could lead to a reactor discontinuity event, such as sheeting, or chunking. Such quieting is believed to be the result of the polymer particles becoming softer as a result of (a) higher temperature or (b) higher concentrations of hydrocarbons dissolved in the polymer particles. It is well known that high concentrations of dissolved hydrocarbons in the resin are the result of high concentrations of condensables in the reactor gas phase, including comonomers and ICAs.

As noted elsewhere herein, with individual grades of polymer produced in gas-phase reactors under condensed mode conditions, each are subject to different operating conditions and will tolerate different levels of ICA(s) and/or comonomer (s), and/or temperature and therefore will have different limiting stickiness thresholds or points. This is due to the effect of the different molecular weights and comonomer incorporation levels of the different grades. To determine an expanded operating window (to increase production rates) by use of acoustic emission sensor(s), the operators of the process, for each given grade, first run the process at steady state in a safe condition (as discussed below) with optimum production conditions. At steady state, the acoustic emissions are recorded. Then, to increase production rate, reactor conditions are changed, such as increasing the catalyst feed rate and/or increasing ICA concentration level and/or increasing reactor temperature. Then the reactor operators monitor the acoustic emissions and when the acoustic emissions drop to a negative deviation of 0.1, or 0.25, or 0.5, or 0.75, or 1, or 2, or 3, or 4, or 5, or 6, or more standard deviations below the acoustic emissions of the relative steady state, "safe" mode level of acoustic emissions, that is as the reactor gets "quieter", as determined by acoustic emission sensors, the operators take corrective action as outlined herein. These standard deviations may also be noted as −1, −2, −3, and so on, standard deviations from the relative steady state "safe" mode. Positive deviations (a noisier reactor) of acoustic emissions from the level of emissions at steady state are not the subject of embodiments of our invention. Acoustic emissions sensors may also be used, as described herein, to determine when stickiness in the reactor is increasing even when no conscious act to increase production may have been taken.

It is the determination of quieting of the reactor, or more specifically the quieting of the contents of the reactor as determined by one or more acoustic emission sensors placed as noted herein, that define increasing levels of stickiness in the reactor.

Acoustic Emissions Sensors

At least one acoustic emission sensor may be located at one or more positions in the vertical or cylindrical section of the reactor, generally above the distributor plate, generally in the fluidized bed section (defined herein) of a reactor, typically a gas-phase reactor. With the at least one acoustic emission sensor (AES), we contemplate 1, 2, 3, 4, 5, 6, 7, 8, 9, 10 or more of these acoustic emission sensors in one or more locations on the vertical/cylindrical section of a reactor, above the distributor plate and below the junction of the cylindrical section and the conical section of the reactor. The one or more acoustic emission sensors are typically located or mounted externally to the reactor. However, in the discussion of the "distributor plate" as a lower limit to the location of one or more acoustic emissions sensors on the exterior of the reactor, it is understood that the actual distributor plate is on the inside of the reactor, and that the use of "above the distributor plate" means above that location as marked on the exterior of the reactor, and measured relative to the top of the distributor plate.

The at least one acoustic emission sensor is essentially a small microphone that can detect and amplify high frequency (ultrasonic) sound waves. The at least one acoustic emission sensor typically utilizes a piezoelectric transducer to detect the acoustic noise generated by the impact of resin particles on the walls surrounding a flowing stream (in this case the fluid bed section of a reactor). The acoustic "noise" is normally measured in the ultrasonic range.

The one or more acoustic emission sensors are narrow bandwidth piezo-electric sensors with local pre-amplifiers producing an industry standard gain of 40 decibels (dB), where 0 dB equates to a 1 microvolt output from the sensor. The pre-amplifier output is further amplified using a series of signal amplifiers with a range of 0 to 48 dB. This produces measurable signals in the range of 1 to 10 volts. The signals were narrow band filtered around the center frequency of 190 kHz using a 100-350 kHz band pass filter.

The frequency of the process rather than the frequency of the sensor is of interest. For this reason, the signal is further conditioned to produce an output proportional to the lower frequency variations in the envelope of the narrow-band acoustic emission signal, typically in the audible range of 0 to 20 kHz. A root mean square filter was used for this conditioning.

Acoustic emission sensors may be provided by Process Analysis & Automation, Ltd. (PAA). However, a distinction must be drawn between the disclosure of the PAA documents (discussed herein) and embodiments of the present invention. The PAA documents suggest only the detection a chunk of 1.5 meters, after the agglomerate has been formed. By contrast, embodiments of the present invention detect conditions of increasing stickiness that, if left unchecked or uncorrected, can cause the formation of polymer chunks or sheets, prior to their formation. Further, the PAA documents suggest that the detection of the polymer chunk (already formed) is indicated by an increase in the acoustic noise, whereas, our findings indicate that the onset of conditions that lead to the chunks (or sheets) is indicated by a decrease in acoustic noise.

Catalysts

All polymerization catalysts including conventional coordinated transition metal catalysts and metallocene catalysts or combinations thereof, are suitable for use in embodiments of the processes of the present invention. Also contemplated are catalysts such as $AlCl_3$, cobalt, iron, palladium, or chromium/chromium oxide or "Phillips" catalysts. The following is a non-limiting discussion of the various polymerization catalysts useful in the invention.

GENERAL DEFINITIONS

As used herein, the phrase "catalyst system" includes at least one "catalyst component" and at least one "activator", alternately at least one cocatalyst. The catalyst system may also include other components, such as supports, and is not limited to the catalyst component and/or activator alone or in combination. The catalyst system may include any number of catalyst components in any combination as described herein, as well as any activator in any combination as described herein.

As used herein, the phrase "catalyst compound" includes any compound that, once appropriately activated, is capable of catalyzing the polymerization or oligomerization of olefins, the catalyst compound comprising at least one Group 3 to Group 12 atom, and optionally at least one leaving group bound thereto.

As used herein, the phrase "leaving group" refers to one or more chemical moieties bound to the metal center of the catalyst component that can be abstracted from the catalyst component by an activator, thus producing the species active towards olefin polymerization or oligomerization. The activator is described further below.

As used herein, in reference to Periodic Table "Groups" of Elements, the "new" numbering scheme for the Periodic Table Groups are used as in the CRC HANDBOOK OF CHEMISTRY AND PHYSICS (David R. Lide ed., CRC Press $81^{st}$ ed. 2000).

As used herein, a "hydrocarbyl" includes aliphatic, cyclic, olefinic, acetylenic and aromatic radicals (i.e., hydrocarbon radicals) comprising hydrogen and carbon that are deficient by one hydrogen. A "hydrocarbylene" is deficient by two hydrogens.

As used herein, the phrase "heteroatom" includes any atom other than carbon and hydrogen that can be bound to carbon. A "heteroatom-containing group" is a hydrocarbon radical that contains a heteroatom and may contain one or more of the same or different heteroatoms. In one embodiment, a heteroatom-containing group is a hydrocarbyl group containing from 1 to 3 atoms selected from the group consisting of boron, aluminum, silicon, germanium, nitrogen, phosphorous, oxygen and sulfur. Non-limiting examples of heteroatom-containing groups include radicals of imines, amines, oxides, phosphines, ethers, ketones, oxoazolines heterocyclics, oxazolines, and thioethers.

As used herein, "heterocyclic" refers to ring systems having a carbon backbone that comprise from 1 to 3 atoms selected from the group consisting of boron, aluminum, silicon, germanium, nitrogen, phosphorous, oxygen and sulfur, unless the heteroatom (non carbon atom) is described.

As used herein, an "alkylcarboxylate", "arylcarboxylate", and "alkylarylcarboxylate" is an alkyl, aryl, and alkylaryl, respectively, that possesses a carboxyl group in any position. Examples include $C_6H_5CH_2C(O)O^-$, $CH_3C(O)O^-$, etc.

As used herein, the term "substituted" means that the group following that term possesses at least one moiety in place of one or more hydrogens in any position, the moieties selected from such groups as halogen radicals (for example, Cl, F, Br), hydroxyl groups, carbonyl groups, carboxyl groups, amine groups, phosphine groups, alkoxy groups, phenyl groups, naphthyl groups, $C_1$ to $C_{10}$ alkyl groups, $C_2$ to $C_{10}$ alkenyl groups, and combinations thereof. Examples of substituted alkyls and aryls includes, but are not limited to, acyl radicals, alkylamino radicals, alkoxy radicals, aryloxy radicals, alkylthio radicals, dialkylamino radicals, alkoxycarbonyl radicals, aryloxycarbonyl radicals, carbamoyl radicals, alkyl- and dialkyl-carbamoyl radicals, acyloxy radicals, acylamino radicals, arylamino radicals, and combinations thereof.

Unless stated otherwise, no embodiment of the present invention is herein limited to the oxidation state of the metal atom "M" as defined below in the individual descriptions and examples that follow.

Metallocene Catalyst Component

The catalyst system useful in embodiments of the present invention include at least one metallocene catalyst component as described herein. Metallocene catalyst compounds are generally described throughout in, for example, 1 & 2 METALLOCENE-BASED POLYOLEFINS (John Scheirs & W. Kaminsky eds., John Wiley & Sons, Ltd. 2000); G. G. Hlatky in 181 COORDINATION CHEM. REV. 243-296 (1999) and in particular, for use in the synthesis of polyethylene in 1 METALLOCENE-BASED POLYOLEFINS 261-377 (2000). The metallocene catalyst compounds as described herein include "half sandwich" and "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom.

Hereinafter, these compounds will be referred to as "metallocenes" or "metallocene catalyst components". The metallocene catalyst component is supported on a support material in an embodiment, and may be supported with or without another catalyst component.

The Cp ligands are one or more rings or ring system(s), at least a portion of which includes π-bonded systems, such as cycloalkadienyl ligands and heterocyclic analogues. The ring (s) or ring system(s) typically comprise atoms selected from the group consisting of Groups 13 to 16 atoms, or the atoms that make up the Cp ligands are selected from the group consisting of carbon, nitrogen, oxygen, silicon, sulfur, phosphorous, germanium, boron and aluminum and combinations thereof, wherein carbon makes up at least 50% of the ring members. Or the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7H-dibenzofluorenyl, indeno[1,2-9]anthrene, thiophenoindenyl, thiophenofluorenyl, hydrogenated versions thereof (e.g., 4,5,6,7-tetrahydroindenyl, or "H$_4$Ind"), substituted versions thereof, and heterocyclic versions thereof.

Group 15-Containing Catalyst Component

One aspect of the present invention includes the use of so called "Group 15-containing" catalyst components as described herein as a desirable catalyst component, either alone or for use with a metallocene or other olefin polymerization catalyst component. Generally, "Group 15-containing catalyst components", as referred to herein, include Group 3 to Group 12 metal complexes, wherein the metal is 2 to 8 coordinate, the coordinating moiety or moieties including at least two Group 15 atoms, and up to four Group 15 atoms. In one embodiment, the Group 15-containing catalyst component is a complex of a Group 4 metal and from one to four ligands such that the Group 4 metal is at least 2 coordinate, the coordinating moiety or moieties including at least two nitrogens. Representative Group 15-containing compounds are disclosed in, for example, WO 99/01460; EP A1 0 893 454; EP A1 0 894 005; U.S. Pat. No. 5,318,935; U.S. Pat. No. 5,889,128 U.S. Pat. No. 6,333,389 B2 and U.S. Pat. No. 6,271,325 B1.

In one embodiment, the Group 15-containing catalyst components useful in embodiments of the present invention include Group 4 imino-phenol complexes, Group 4 bis(a-mide) complexes, and Group 4 pyridyl-amide complexes that are active towards olefin polymerization to any extent.

Activator

As used herein, the term "activator" is defined to be any compound or combination of compounds, supported or unsupported, which can activate a single-site catalyst compound (e.g., metallocenes, Group 15-containing catalysts), such as by creating a cationic species from the catalyst component. Typically, this involves the abstraction of at least one leaving group (X group in the formulas/structures above) from the metal center of the catalyst component. The catalyst components of embodiments of the present invention are thus activated towards olefin polymerization using such activators. Embodiments of such activators include Lewis acids such as cyclic or oligomeric poly(hydrocarbylaluminum oxides) and so called non-coordinating activators ("NCA") (alternately, "ionizing activators" or "stoichiometric activators"), or any other compound that can convert a neutral metallocene catalyst component to a metallocene cation that is active with respect to olefin polymerization.

It is within the scope of this invention to use Lewis acids such as alumoxane (e.g., "MAO"), modified alumoxane (e.g., "MMAO"), and alkylaluminum compounds as activators, and/or ionizing activators (neutral or ionic) such as tri (n-butyl)ammonium tetrakis(pentafluorophenyl)boron and/or a trisperfluorophenyl boron metalloid precursors to activate metallocenes described herein. MAO and other aluminum-based activators are well known in the art. Ionizing activators are well known in the art and are described by, for example, Eugene You-Xian Chen & Tobin J. Marks, *Cocatalysts for Metal-Catalyzed Olefin Polymerization: Activators, Activation Processes, and Structure-Activity Relationships* 100(4) CHEMICAL REVIEWS 1391-1434 (2000). The activators may be associated with or bound to a support, either in association with the catalyst component (e.g., metallocene) or separate from the catalyst component, such as described by Gregory G. Hlatky, *Heterogeneous Single-Site Catalysts for Olefin Polymerization* 100(4) CHEMICAL REVIEWS 1347-1374 (2000).

Ziegler-Natta Catalyst Component

The catalyst composition may comprise a catalyst component, which is (or includes) a non-metallocene compound. In an embodiment, the catalyst component comprises a Ziegler-Natta catalyst compound, such as disclosed in ZIEGLER CATALYSTS 363-386 (G. Fink, R. Mulhaupt and H. H. Brintzinger, eds., Springer-Verlag 1995); or in EP 103 120; EP 102 503; EP 0 231 102; EP 0 703 246; RE 33,683; U.S. Pat. No. 4,302,565; U.S. Pat. No. 5,518,973; U.S. Pat. No. 5,525,678; U.S. Pat. No. 5,288,933; U.S. Pat. No. 5,290,745; U.S. Pat. No. 5,093,415 and U.S. Pat. No. 6,562,905. Examples of such catalysts include those comprising Group 4, 5 or 6 transition metal oxides, alkoxides and halides, or oxides, alkoxides and halide compounds of titanium, zirconium or vanadium; optionally in combination with a magnesium compound, internal and/or external electron donors (alcohols, ethers, siloxanes, etc.), aluminum or boron alkyl and alkyl halides, and inorganic oxide supports.

Conventional-type transition metal catalysts are those traditional Ziegler-Natta catalysts that are well known in the art. Any reference herein to Ziegler-Natta catalysts are to these "traditional" or "conventional" type catalysts. (Ref: J. Boor, "Ziegler-Natta Catalysts and Polymerizations", Academic Press (1979)) Examples of conventional-type transition metal catalysts are discussed in U.S. Pat. Nos. 4,115,639, 4,077,904, 4,482,687, 4,564,605, 4,721,763, 4,879,359 and 4,960,741. The conventional-type transition metal catalyst compounds that may be used in the present invention include transition metal compounds from Groups 3 to 17, or Groups 4 to 12, or Groups 4 to 6 of the Periodic Table of Elements.

These conventional-type transition metal catalysts may be represented by the formula: $MR_x$, where M is a metal from Groups 3 to 17, or a metal from Groups 4 to 6, or a metal from Group 4, or titanium; R is a halogen or a hydrocarbyloxy group; and x is the valence of the metal M. Examples of R include alkoxy, phenoxy, bromide, chloride and fluoride. Examples of conventional-type transition metal catalysts where M is titanium include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_2H_5)_2Br_2$, $TiCl_3 \cdot \frac{1}{3}AlCl_3$ and $Ti(OC_{12}H_{25})Cl_3$.

Conventional-type transition metal catalyst compounds based on magnesium/titanium electron-donor complexes that are useful in embodiments of the invention are described in, for example, U.S. Pat. Nos. 4,302,565 and 4,302,566. Catalysts derived from Mg/Ti/Cl/THF are also contemplated, which are well known to those of ordinary skill in the art. One example of the general method of preparation of such a catalyst includes the following: dissolve $TiCl_4$ in THF, reduce the compound to $TiCl_3$ using Mg, add $MgCl_2$, and remove the solvent.

Conventional-type cocatalyst compounds for the above conventional-type transition metal catalyst compounds may be represented by the formula $M^3M^4_vX^2_cR^3_{b-c}$, wherein $M^3$ is a metal from Group 1 to 3 and 12 to 13 of the Periodic Table of Elements; $M^4$ is a metal of Group 1 of the Periodic Table of Elements; v is a number from 0 to 1; each $X^2$ is any halogen; c is a number from 0 to 3; each $R^3$ is a monovalent hydrocarbon radical or hydrogen; b is a number from 1 to 4; and wherein b minus c is at least 1. Other conventional-type organometallic cocatalyst compounds for the above conventional-type transition metal catalysts have the formula $M^3R^3_k$, where $M^3$ is a Group IA, IIA, IIB or IIIA metal, such as lithium, sodium, beryllium, barium, boron, aluminum, zinc, cadmium, and gallium; k equals 1, 2 or 3 depending upon the valency of $M^3$ which valency in turn normally depends upon the particular Group to which $M^3$ belongs; and each $R^3$ may be any monovalent radical that include hydrocarbon radicals and hydrocarbon radicals containing a Group 13 to 16 element like fluoride, aluminum or oxygen or a combination thereof.

Polymerization

Polymerization may be conducted using the above catalysts and monomers selected from ethylene and one or more α-olefins selected from propylene, 1-butene, 1-hexene, 4-methyl-1-pentene, 1-octene or 1-decene.

In order to provide a better understanding of the present invention, the following examples are offered as related to actual tests performed in the practice of the invention:

EXAMPLES

The polymerization reactions described herein were conducted in a continuous pilot-scale gas phase fluidized bed reactor of 0.57 meters internal diameter and 4.0 meters in bed height. The fluidized bed was made up of polymer granules. The gaseous feed streams of ethylene and hydrogen together with liquid comonomer were mixed together in a mixing tee arrangement and introduced below the reactor bed into the recycle gas line. Hexene was used as comonomer. The individual flow rates of ethylene, hydrogen and comonomer were controlled to maintain fixed composition targets. The comonomer was also controlled to maintain a constant comonomer to ethylene mole ratio. The ethylene concentration was controlled to maintain a constant ethylene partial pressure. The hydrogen was controlled to maintain a constant hydrogen to ethylene mole ratio. The concentrations of all the gases were measured by an on-line gas chromatograph to ensure relatively constant composition in the recycle gas stream.

The solid catalyst was injected directly into the fluidized bed using purified nitrogen as a carrier. The catalyst feed rate was adjusted to maintain a constant production rate. The reacting bed of growing polymer particles was maintained in a fluidized state by the continuous flow of the make up feed and recycle gas through the reaction zone. A superficial gas velocity of 0.6-0.9 meters/sec was used to achieve this. The reactor was operated at a total pressure of 2170 kPa. To maintain a constant reactor temperature, the temperature of the recycle gas entering the reactor was continuously adjusted up or down to accommodate any changes in the rate of heat generation due to the polymerization.

The fluidized bed was maintained at a constant height (4.0 meters) by withdrawing a portion of the bed at a rate equal to the rate of formation of particulate product. The rate of product formation (the polymer production rate) was in the range of 50-70 kg/hour. The product was removed semi-continuously via a series of valves into a fixed volume chamber, which was simultaneously vented back to the reactor. This allows for highly efficient removal of the product, while at the same time recycling a large portion of the unreacted gases back to the reactor. This product was purged to remove entrained and dissolved hydrocarbons and treated with a small steam of humidified nitrogen to deactivate any trace quantities of residual catalyst.

FIG. 1 is a schematic of the pilot-scale fluidized bed reactor and the approximate locations of the acoustic measuring instruments.

Readings from the AES were measured in the form of volts. Data from multiple probes were collected simultaneously using a PC based data acquisition system. Data from each probe were collected at 100 readings/second. The data was continuously monitored, and an average value was logged every 60 seconds for plotting purposes. Data reported from four different acoustic emission sensors located at various points on the reactor were recorded in a computer log, and used to generate the plots shown in FIGS. 2-4.

FIG. 2 shows the results of a pilot plant test, in which the reactor was purposely driven to the sticking limit by first lowering the resin density by increasing the hexene comonomer to ethylene molar ratio, then adding an ICA (isopentane) and then finally gradually increasing temperature. The comonomer to ethylene mole ratio was increased from 0.024 to 0.029 resulting in a decrease in the polymer density from 0.9167 to 0.9113 g/cc. The isopentane was then increased from 0 to 6.8 mole percent. This was followed by an increase in the reactor temperature set point from 175° F. (79.4° C.) in a series of 5° F. (2.7° C.) increments each hour. Note: due to specific constraints peculiar to this specific reactor, the addition of ICA and lowering of density were not individually sufficient to drive the polymer to the sticking point (although, if pushed further, each of these variables could have individually driven the polymer to the sticking point). Therefore the third variable, reactor temperature was necessary to arrive at the limiting sticking point in these experiments. These steps (adding ICA, increasing the comonomer concentration, then increasing reactor temperature) were taken sequentially. When the indicated bed temperature was 189.7° F. (87.6° C.), readings from two of three acoustic emission sensors, located 15.24 cm or 0.267 reactor diameters and 167.6 cm or 2.93 diameters above the distributor plate began to decrease, and the third sensor located on the overhead recycle line began to increase. As the temperature increase continued, the readings from these three sensors continued to exhibit this behavior as shown in FIG. 2. In contrast, the fluidized bulk density based on differential pressure reading decreased only slightly during this time, as also seen in FIG. 2. The drop in fluidized bulk density eventually became more pronounced, but this did not occur until shortly before a chunk formed (14 hours after. the start of the temperature ramp). We have found that the problem with fluidized bulk density (FBD) as determined by differential pressure (DP) cells (besides the "slow" response) is that it is essentially non-linear in its response to increasing stickiness, showing limited response until just before fluidization is lost. In this example, the FBD signal is initially weak and the signal becomes stronger only at the ultimate limit of ICA concentration is reached as the temperature was increased. Had this been an actual commercial operation, the operators likely would not have noticed the slight drop in FBD reading and would have continued to feed isopentane at a high rate, or continued to increase reactor temperature, driving the fluidized bed closer to the sticking limit. Therefore the FBD would not have provided a substantial meaningful indication of reactor trouble until just before the fluid bed became too sticky and possibly sintered (creating a chunk).

The experimental data provides some important and unexpected results. When the reactor temperature was increased in combination with lower resin density and ICA agent (isopentane) being present, the polymer bed was forced from a condition of smooth particulate fluidization to a point of excessive (or limiting) stickiness where particles began to sinter. This became progressively worse, and the bed reached its sticking point, which finally resulted in a fused mass of polymer and the formation of solid chunk. All the conventional sensors were able to detect the eventual chunking point, but the points in time at which the detection occurred were very different. Significant shifts in the instrument readings took place on the acoustic emission sensors 6½ hours, on the dP sensors 2½ hours and on the skin thermocouples 40 minutes prior to the actual shutdown. The advanced warning of 6½ hours is significant and would allow an operator to make several adjustments to prevent the point of limiting stickiness by adjusting the fluidization of the bed away from this point. This also will allow for optimization of the reactor production rate to match it to the ultimate reactor capacity.

While embodiments of the present invention have been described and illustrated by reference to particular embodiments, it will be appreciated by those of ordinary skill in the art that embodiments of the invention lend themselves to variations not necessarily illustrated herein. For this reason, then, reference should be made solely to the appended claims for purposes of determining the true scope of the present invention

What is claimed is:

1. A process for operating a gas-phase reactor at or near maximum production rates, under condensed mode reactor conditions, comprising:
   a) feeding monomers and at least one catalyst to the gas-phase reactor, to make polymer particles;
   b) feeding at least one induced condensing agent (ICA) to the gas-phase reactor;
   c) measuring an acoustic emission signal or signals the polymer particles in the gas-phase reactor using at least one acoustic emission sensor;
   d) processing the signal or signals by arithmetic averaging the acoustic emission signal or signals sampled over a time window in the range of 0.001-1000 seconds, where the sampling frequency ranges from 0.01-1000 samples per second; and
   e) controlling the reactor at or near maximum production rate for a given polymer, by the measuring the acoustic emission signal or signals, such that when the acoustic emission signal or signals deviate from the arithmetic average acoustic emission signal or signals of a steady state reactor producing the same given polymer, by more than three negative standard deviation, the controlling comprises a corrective action comprising: adjusting one of ICA level, comonomer level, reactor temperature or combinations thereof.

2. The process of claim 1, wherein the at least one acoustic emission sensor (AES) is located on an exterior cylindrical section of the reactor, at a location on the cylindrical section between a point above a reactor distributor plate, and/or below a cylindrical-cortical junction of the reactor.

3. The process of claim 2, wherein the at least one AES is located on the exterior of the reactor, at a point that excludes the first 0.25 reactor diameters above a reactor distributor plate, and/or that excludes the first 0.25 reactor diameters below a cylindrical-conical junction of the reactor.

4. The process of claim 3, wherein the process comprises a catalyst selected from one of Ziegler-Natta, chromium, chromium oxide, AlCl$_3$, cobalt, iron, palladium, or a metallocene catalyst.

5. The process of claim 3, wherein the catalyst comprises a metallocene catalyst.

6. The process of claim 4, wherein the monomers comprise ethylene and one or more α-olefins.

7. The process of claim 6, wherein the α-olefins comprise one or more of 1-butene, 1-hexene, or 1-octene.

8. The process of claim 4 or 5, wherein when the acoustic emission signal or signals negatively deviate from the arithmetic average steady state acoustic emission signal or signals by four or more standard deviations from the steady state acoustic emission signal or signals, the corrective action is taken.

9. The process of claim 4 or 5, wherein when the acoustic emission signal or signals comprise negative deviations from the steady state acoustic emission by five or more standard deviations from the steady state acoustic emission signal or signals, the corrective action is taken.

10. The process of claim 4 or 5, wherein the processing of the signal or signals comprises arithmetic averaging using acoustic emissions signal or signals sampled from a time window in the range of 1-500 seconds, where the sampling frequency ranges from 1-500 samples per second.

11. A process of producing an ethylene copolymer in a gas phase reactor at or near maximum production rates for the ethylene copolymer, comprising:
   maintaining a signal or signals of one or more acoustic emissions sensors located on a cylindrical section of the reactor, in the range of zero to minus three (−3) standard deviations of the arithmetic averages of signals produced by said sensors, at steady state conditions in the reactor the improvement comprising taking corrective action when the signal or signals deviate negatively by more than three standard deviations from the arithmetic average of the steady state values; the corrective action comprising adjusting one of ICA level, comonomer level, reactor temperature or combinations thereof.

12. The process of claim 11, wherein the process further comprises feeding a metallocene catalyst to the reactor, and wherein the ethylene copolymer comprises ethylene and one or more of propylene, 1-butene, 1-hexene, 1-pentene, 4-methyl-1-pentene, 1-octene or 1-decene.

13. A method of optimizing the space time yield in a gas-phase, fluidized bed reactor, comprising:
   a) feeding to the reactor:
      i) a metallocene catalyst;
      ii) one or more of an ionic activator, an alumoxane or a modified alumoxane;
      iii) ethylene and a comonomer selected from one or more of 1-butene, 1-hexene, or 1-octene to form a polymer;
   b) feeding an induced condensing agent (ICA) to the reactor;
   c) monitoring a signal or signals from at least one acoustic emission sensor (AES), the at least one AES being located on an exterior of a cylindrical section of the reactor, at a point that excludes the first 0.25 reactor diameters above a reactor distributor plate, and/or that excludes the first 0.25 reactor diameters below a cylindrical-conical junction of the reactor, processing of the signal or signals comprises arithmetic averaging using the acoustic emissions signal or signals sampled from a time window in the range of 0.01-1000 seconds, where the sampling frequency ranges from 0.01-1000 samples per second; and d) adjusting one of ICA level, comonomer level, reactor temperature or combinations thereof, when the signal or signals comprises negative deviations of more than three standard deviations from an acoustic signal or signals of the process at steady state conditions when producing the same reactor polymer.

14. A process for monitoring stickiness of polymer particles in a gas-phase, fluid-bed polymerization reactor, comprising:

a) feeding ethylene and a comonomer selected from one or more of 1-butene, 1-hexene or 1-octene and a metallocene catalyst; one or more of an ionic activator, an alumoxane or a modified alumoxane, to the reactor, b) feeding an induced condensing agent (ICA) to the reactor;

c) measuring acoustic emission signal or signals of the particles using at least one acoustic emission sensor on the exterior of the reactor, wherein the at least one acoustic emission sensor is located on an exterior cylindrical section of the reactor, at a point between the first 0.25 reactor diameters above a reactor distributor plate, and below the first 0.25 reactor diameters below a cylindrical-conical junction of the reactor, wherein processing the signals comprises using an arithmetic averaging using the acoustic emissions signal or signals sampled from a time window in the range of 0.01-1000 seconds, where the sampling frequency ranges from 0.01-1000 samples per second; and d) adjusting one of ICA level, comonomer level, reactor temperature or combinations thereat when the arithmetic average of said signal or signals deviates more than three standard deviations negatively from an arithmetic average of an acoustic signal or signals of the process at steady state conditions when producing the same reactor polymer.

* * * * *